United States Patent [19]

Feldstein et al.

[11] 4,249,417
[45] Feb. 10, 1981

[54] MULTIFUNCTIONAL TRANSDUCER

[76] Inventors: Alan M. Lovelace, Administrator of the National Aeronautics and Space Administration, with respect to an invention of Cyril Feldstein, Sierra Madre, Calif.; Gilbert W. Lewis, Arcadia, Calif.; Virgil H. Culler, La Canada, Calif.; Samuel Merrbaum, Woodland Hills, Calif.

[21] Appl. No.: 44,432

[22] Filed: Jun. 1, 1979

[51] Int. Cl.³ .............................................. G01L 5/00
[52] U.S. Cl. .................................. 73/141 A; 128/642; 128/774
[58] Field of Search ................... 73/141 A, 781, 794, 73/760; 128/774, 782, 642; 338/6

[56] References Cited

U.S. PATENT DOCUMENTS

| | | | |
|---|---|---|---|
| 2,815,424 | 12/1957 | Painter | 73/781 |
| 3,905,356 | 9/1975 | Fletcher et al. | 73/781 |
| 3,937,212 | 2/1976 | Fletcher et al. | 73/781 |
| 3,971,363 | 7/1976 | Fletcher et al. | 128/695 |
| 3,995,476 | 11/1976 | Hoffman | 73/133 R |
| 4,058,005 | 11/1977 | Barnett | 73/781 |
| 4,204,544 | 5/1980 | Feldstein et al. | 73/781 |

*Primary Examiner*—Donald O. Woodiel
*Attorney, Agent, or Firm*—Monte F. Mott; John R. Manning; Paul F. McCaul

[57] ABSTRACT

A transducer is described for simultaneously measuring several parameters of a small region of a muscle tissue or other object, with minimal traumatizing or damage of the object. A trifunctional transducer which can measure the force applied by a muscle fiber, the displacement of the fiber, and the change in thickness of the fiber, includes a device having three legs with inner ends joined together and outer ends formed to pierce the tissue and lie therein. Two of the legs are relatively stiff, to measure force applied by the tissue, and a third leg is relatively flexible to measure displacement of the tissue relative to one or both stiff legs, and with the three legs lying in a common plane so that the force and displacement measurements all relate to the same direction of muscle movement. A flexible loop is attached to one of the stiff legs to measure changes in muscle thickness, with the upper end of the loop fixed to the leg and the lower end of the loop bearing against the surface of the tissue and being free to slide on the leg.

2 Claims, 3 Drawing Figures

MULTIFUNCTIONAL TRANSDUCER

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

The analysis of certain objects, including biological objects such as muscle tissue and inanimate objects such as rocket fuel, can be enhanced by apparatus that enables the measurement of multiple parameters to be conducted at subtantially the same area of the object, with all parameters measured simultaneously, and with minimal disturbance of the object. For example, a major thrust of heart research is directed toward assessment of regional myocardial mechanics. This research activity is limited by the availability of suitable transducers to record dynamic activity. Measurements of the force applied by the tissue, the displacement resulting from the application of the force, and the change in thickness of the tissue resulting from the application of force and the resulting displacement, are a group of parameters whose measurement can be valuable in analyzing the mechanics of tissue function. Individual transducers have been proposed for measuring at least certain of these parameters. For example, U.S. Pat. No. 3,937,212 by Feldstein et al describes a transducer for measuring displacement of muscle tissue, while U.S. Pat. No. 3,971,363 by Feldstein et al describes a transducer for measuring changes in the thickness of muscle tissue. However, the use of several separate devices for measuring different parameters has several disadvantages. One disadvantage is that it is difficult to position all of the devices very close to one another so as to enable measurements of substantially the same tissue region, and it is difficult accurately to emplace the different devices in a particular relationship so as to insure measurement of different parameters of the same phenomenon. Also, the use of separate devices, each with a separate one or pair of prongs to be inserted into the tissue or other object, results in excessive trauma or damage to the object.

SUMMARY OF THE INVENTION

In accordance with one embodiment of the present invention, a multifunctional transducer is provided, which enables the measurement of a plurality of parameters of an object simultaneously, over a very small region, and with minimal trauma to the object. A transducer which is designed to measure stress and strain near the surface of an object such as in muscle tissue, includes a device having three legs with inner ends connected together and outer ends that can be fixed to the object as by inserting them into the muscle tissue. The outer ends of the three legs lie substantially in the same plane, to measure force and resulting displacement along substantially the same direction. One pair of legs are substantially noncompliant, or stiff, so that the change in their separation resulting from a force applied by the tissue, is only a minority of the change that would occur if one or both legs were highly compliant. Accordingly, slight bending of the legs indicates the force applied by the tissue, which they resist. A third leg is compliant, or flexible, to be easily displaced by the tissue so as to indicate the unobstructed displacement of the tissue which results from the application of the force measured by the other two legs. Thus, only three legs puncture the tissue or other object to minimize trauma to it and enable measurements to be made over a very small region of the tissue, and accurate alignment of the legs can be easily accomplished to assure measurement of stress and strain along the same direction.

The change in thickness of the object such as muscle tissue, can be measured by a compliant loop with one end fixed to one of the legs and the other end pressing against the surface of the tissue and slidable along the same leg. Accordingly, the same leg utilized to measure stress and/or strain, also serves to hold one end of the thickness-measuring loop to avoid additional trauma to the tissue, while also assuring that thickness is measured at the same region at which stress and strain are measured.

The novel features of the invention are set forth with particularity in the appended claims. The invention will be best understood from the following description when read in conjunction with the accompanying drawings.

DESCRIPTION OF THE PREFERRED EMBODIMENT

Figure 1:
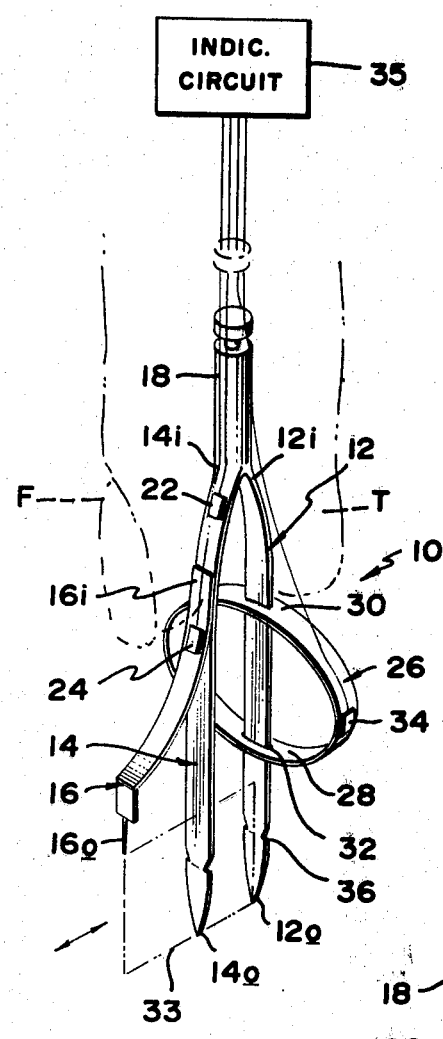
FIG. 1 is a perspective view of a multifunctional transducer constructed in accordance with an embodiment of the invention.

FIG. 1 illustrates a trifunctional transducer 10 that can be utilized to measure simultaneously, the force, displacement and thickness within a muscle fiber. The device includes three legs 12, 14, and 16 with inner ends 12i–16i that are joined together and outer ends 12o–16o that are free and that have pointed tips to fix them in position in tissue whose parameters are to be measured. The device includes a shank 18 that can be grasped by the thumb T and another finger F of an operator, to install the trifunctional transducer in tissue.

Figure 2:
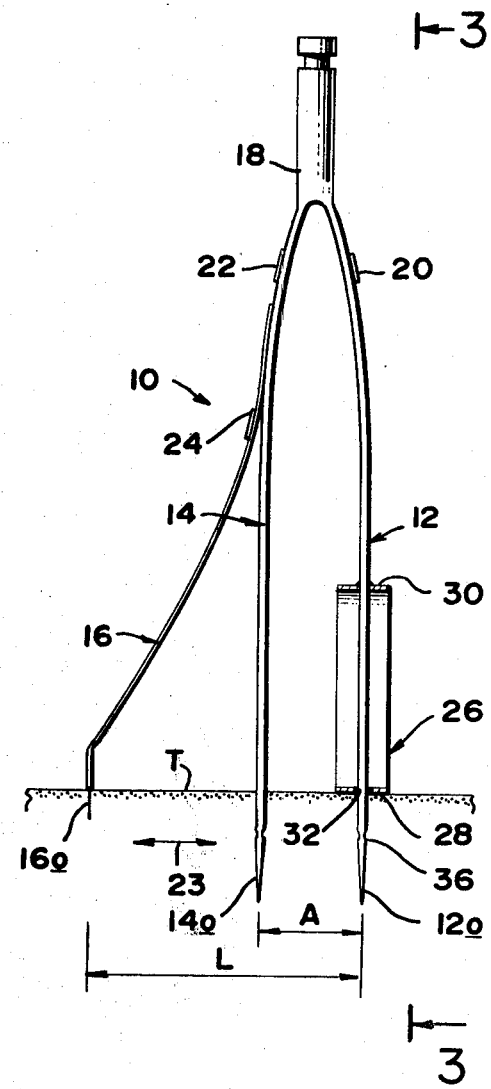
FIG. 2 is a side elevation view of the transducer of FIG. 1, shown implanted in tissue.
Figure 3:
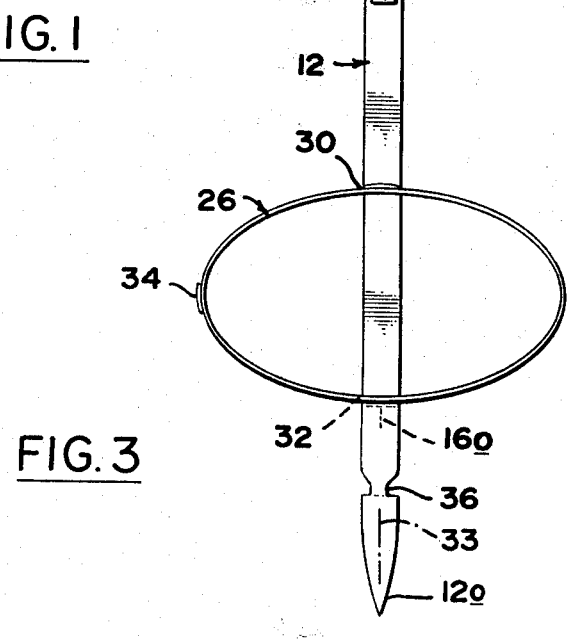
FIG. 3 is a view taken on the line 3—3 of FIG. 2.

FIG. 2 shows the transducer 10 installed in tissue T such as a muscle fiber, to measure stress and strain thereof. Two of the legs 12, 14 of the device are relatively noncompliant, or stiff, to resist bending together and apart, although they undergo a small but measurable degree of bending when forces are applied in the range that can be produced by the muscle tissue. Although the force applied by the tissue would normally (in the absence of the device 10) cause considerable change in the distance A between the leg outer ends, the stiffness of the legs 12, 14 permits only a small change in this distance A. A pair of strain gage sensing elements 20, 22 attached to the legs measures slight bending of them, which indicates the amount of force applied by the tissue to the outer ends of the legs, to thereby enable a determination of the force applied by the tissue.

The third leg 16 of the device has an inner end 16i fixed to one of the noncompliant legs 14 and an outer end or tip 16o which is installed in the tissue T. The leg 16 is highly compliant, or flexible, so that it will easily bend to permit movement of its outer end 16o to follow normal movement of the muscle tissue, in the direction of arrows 23. The high compliance of the leg 16 results in its outer end 16o producing minimal retardation of normal muscle displacement in the absence of the leg. Thus, a strain gage sensing element 24 attached to the leg 16, measures bending of it which indicates the displacement of the tissue at the point engaged by the leg tip 16o with relation to the tissue location engaged by the other leg tip 14o.

In order to enable measurement of changes of the thickness of muscle tissue, a compliant loop 26 is provided, which has one free end 28 bearing against the tissue T and an opposite fixed end 30 which is fixed to the device along one of the noncompliant legs 12. The loop 26 is shown as a continuous elliptical loop, although a noncontinuous loop can be utilized. The loop can be mounted by providing a hole 32 at its outer end that permits it to slide freely along the leg 12, and by brazing its inner end 30 to another portion of the leg. A sensing element 34 (FIG. 1) attached to the loop 26 enables measurements of bending thereof, and therefore of thickening and thinning of the tissue T (FIG. 2) with respect to the point of indentation of the tip end of the arm 12.

The multifunction transducer 10 enables the measurement of stress, strain, and thickness change of a small area of the muscle tissue, with minimal trauma to it. The leg 12 which serves to measure forces applied by the tissue between it and another leg 14, also serves to support the loop 26 that measures changes in tissue thickness. The leg 14 which operates with leg 12 to measure forces also serves as a location to which the distance of the compliant leg end 26o can be measured. The fact that the leg 16 is fastened to the same structure as the other legs 12, 14, assures that its outer end 16o can lie in substantially the same plane, indicated at 33, as the outer ends 12o, 14o of the other arms. As a result, the displacement measurement (between the arm ends 14o, 16o) is taken along the same direction as the force measurement obtained by measuring slight displacements between the outer ends 12o, 14o of the other two arms. The fact that each of the arms 12, 14 serves two functions, not only minimizes the number of punctures of the tissue, but also enables all measuring locations, such as of the member ends 12o, 14o, 16o, and 28 to be located very close together. This avoids errors that can result where devices measuring different parameters are spaced further apart, so that a displacement or thickness measurement may not closely correspond to the measured force applied by the tissue.

The four strain gage sensing elements 20, 22, 24 and 34, can each be provided with a pair of thin wires that can be connected to a parameter indicating circuit 35 such as resistance-measuring bridges of well known types, which can be calibrated to convert measured resistance changes to changes in the relative displacements of the ends of the arms or loops or the forces producing the changes. The two noncompliant arms 12, 14 are utilized as the main anchors for the device, and can be formed with indentations, such as those provided by recesses 36, to securely anchor them to the tissue. The outer ends of these arms 12, 14 extend beyond the ends 16o and 28 of the flexible arm and flexible loop, to enable them to be planted deeply enough into the tissue to hold them in place.

In one multifunction transducer of the illustrated type which has been constructed, the device had an overall length L between its outer ends that engage the tissue, of about four millimeters, and was effective in measuring parameters of muscle tissue over a region such as 4 mm by 1.5 mm. The fact that all of the multiple measuring device ends are fastened together, facilitates, implantation of the device in tissue. The device was utilized to measure dynamic conditions in heart muscles.

Thus, the invention provides a multifunction transducer which can be utilized to measure the force and corresponding displacement of an object such as muscle tissue, in a small region of the object and with minimal trauma or damage to the object, in a device that facilitates accurate relative positioning of different parts that contact the object. This can be accomplished by utilizing a device with a pair of relatively noncompliant legs having inner ends joined together and outer ends that can be fixed in position relative to the object, and by providing a compliant leg with an inner end fixed relative to at least one of the noncompliant legs and an outer end that can also engage the object. The three legs can be positioned so their outer ends lie substantially in the same plane, so that force and displacement are measured along substantially the same direction. Thickness measurement also can be provided for, at substantially the same small area of the object and without requiring further traumatization of it, by the use of a compliant loop with an inner end fixed to one of legs and an outer end slidable relative to the leg and bearing against the surface of the object.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. A transducer comprising:
   a pair of legs having inner ends joined together and pointed outer ends for penetrating into an object;
   a loop having one portion fixed to a predetermined one of said legs and an opposite portion free to slide relative to said predetermined leg; and
   means for sensing relative movement of said legs, and relative movement of said opposite portions of said loop.

2. A transducer for measuring stress and strain near the surface of an object, comprising:
   three legs having free outer ends and connected inner ends, said leg outer ends having means for fixing them in position with respect to the object so the legs move in response to movement of the object locations to which they are fixed;
   first sensor means for measuring relative movement of a first pair of said legs;
   second sensor means for measuring relative movement of a second pair of said legs;
   said first pair of legs being stiff against movement of their outer ends, and one of said legs of said second pair being highly compliant to movement of its outer ends; and
   a thickness measuring device including a compliant loop having a first portion fixed to one of said legs and a second free portion which can move relative to said leg, and sensing means for measuring bending of the loop, whereby to measure changes in thickness at the same region of the object where stress and strain are measured.

* * * * *